United States Patent [19]
Ayer et al.

[11] Patent Number: 6,096,339
[45] Date of Patent: Aug. 1, 2000

[54] DOSAGE FORM, PROCESS OF MAKING AND USING SAME

[75] Inventors: Atul D. Ayer, Palo Alto; Andrew Lam, San Francisco; Judy A. Magruder; Lawrence G. Hamel, both of Mountain View; Patrick S. L. Wong, Palo Alto, all of Calif.

[73] Assignee: ALZA Corporation, Mountain View, Calif.

[21] Appl. No.: 08/826,642

[22] Filed: Apr. 4, 1997

[51] Int. Cl.[7] .............................. A61K 9/22; A61K 9/24
[52] U.S. Cl. ........................ 424/473; 424/468; 424/469; 424/470; 424/464
[58] Field of Search ..................... 424/473, 484, 424/469, 468, 470; 604/890.1, 892.1; 514/964

[56] References Cited

U.S. PATENT DOCUMENTS

| | | | |
|---|---|---|---|
| 3,845,770 | 11/1974 | Theeuwes et al. | 128/260 |
| 4,093,709 | 6/1978 | Choi et al. | 424/19 |
| 4,318,400 | 3/1982 | Peery et al. | 128/214 F |
| 4,327,725 | 5/1982 | Cortese et al. | 128/260 |
| 4,612,008 | 9/1986 | Wong et al. | 604/892 |
| 4,765,989 | 8/1988 | Wong et al. . | |
| 4,783,337 | 11/1988 | Wong et al. | 424/468 |
| 4,842,867 | 6/1989 | Ayer et al. | 424/473 |
| 4,863,744 | 9/1989 | Urquhart et al. | 424/484 |
| 4,915,954 | 4/1990 | Ayer et al. | 424/473 |
| 4,946,685 | 8/1990 | Edgren et al. | 424/472 |
| 4,946,687 | 8/1990 | Ayer et al. | 424/473 |
| 4,948,592 | 8/1990 | Ayer et al. | 424/473 |
| 4,950,486 | 8/1990 | Ayer et al. | 424/473 |
| 4,966,769 | 10/1990 | Guittard et al. | 424/473 |
| 5,019,396 | 5/1991 | Ayer et al. . | |
| 5,098,714 | 3/1992 | Wright et al. | 424/473 |

FOREIGN PATENT DOCUMENTS

| | | |
|---|---|---|
| 0 238 189 A1 | 9/1987 | European Pat. Off. ......... A61K 9/22 |
| 0 347 024 A2 | 12/1989 | European Pat. Off. ......... A61K 9/32 |
| 0 378 404 | 7/1990 | European Pat. Off. . |
| 0 378 404 A2 | 7/1990 | European Pat. Off. ....... A61M 31/00 |
| 1 503 116 | 7/1976 | United Kingdom . |
| 92/04011 | 3/1992 | WIPO . |
| WO 92/04011 | 3/1992 | WIPO .............................. A61K 9/22 |

OTHER PUBLICATIONS

Andreotti, Felicita et al. 1988 "Major Circadian Fluctuations in Fibrinolytic Factors and Possible Relevance to Time of Onset of Myocardial Infarction, Sudden Cardiac Death and Stroke" Am Jour Cardio. vol.62, pp. 635–637.

Braunwald, Eugene 1988 Heart Disease, A Textbook of Cardiovascular Medicine. vol. 2 pp. 1234–1235. W.B. Saunders Co., Philadelphia PA.

Ridker, Paul M. et al. 1990 "Circadian Variation of Acute Myocardial Infarction and the Effect of Low–Dose Aspirin in a Randomized Trial of Physicians" Circulation, vol. 82, pp. 897–902.

Wurster, Dale E. 1959 "Air–suspension Technique of Coating Drug Particles" Jour Am Pharm Assoc, vol. 48, No. 8, pp. 451–454.

*Primary Examiner*—Thurman K. Page
*Assistant Examiner*—Brian K. Seidleck
*Attorney, Agent, or Firm*—Paul L. Sabatine; Susan K. Thomas

[57] ABSTRACT

The invention disclosed pertains to a dosage form comprising an agent formulation comprising drug and pharmaceutical carrier of cooperating particle size and means for dispensing the agent formulation from the dosage form.

31 Claims, 3 Drawing Sheets

DOSAGE FORM, PROCESS OF MAKING AND USING SAME

FIELD OF THE INVENTION

This invention pertains to a dosage form that provides a delivery of drug over an extended period of time. More particularly, the invention concerns a dosage form that provides a known and constant drug-release pattern for an indicated therapy. The invention also relates to a dosage form that provides a controlled, constant and uniform delivery of a known dose of drug over time.

BACKGROUND OF THE INVENTION

A critical need exists for a dosage form for the controlled and uniform administration of a drug for therapy over time. Presently, in the practice of pharmacy and medicine a drug is administered in conventional pharmaceutical forms, such as tablets and capsules. These conventional forms deliver their drug by dumping, which leads to uneven dosing of drug and uneven blood levels of drug, characterized by peaks and valleys. Accordingly, this does not provide controlled and uniform therapy over time.

The prior art provides dosage forms for continuous therapy. For example, in U.S. Pat. No. 4,327,725, issued to Cortese and Theeuwes, and in U.S. Pat. Nos. 4,612,008, 4,765,989 and 4,783,337, issued to Wong, Barclay, Deters and Theeuwes, a dosage form is disclosed that provides therapy by generating an osmotic pressure inside the dosage form. The dosage form of these patents operates successfully for delivering a drug for a preselected therapy. With the delivery of some drugs, however, these dosage forms often exhibit erratic release rate patterns, such as a non-uniform variation in the drug release rate, and the dosage form can stop delivering a drug; that is, the dosage form can shut down intermittently.

In view of the above presentation, it is immediately apparent that an urgent need exists for a reliable dosage form. The need exists for a dosage form endowed with properties for delivering a drug at a known and uniform rate over time. The need also exists for a dosage form free of deviation in its release-rate profile, which delivers the needed dose of drug with a reduced amount of drug left in the dosage form at the end of the delivery period. It will be appreciated by those knowledgeable in the drug-dispensing art that if a novel and unexpected dosage form is made available that provides a uniform and known drug-release profile free of the tribulations of the prior art, such a dosage form would represent an advancement and a valuable contribution in the drug dispensing art.

OBJECTS OF THE INVENTION

Accordingly, in view of the above presentation it is an immediate object of the invention to provide a dosage form that delivers a drug in an uniform dose to a biological, drug-receiving environment over an extended drug-delivery therapy time.

Another object of the invention is to provide a novel dosage form that avoids administering a drug in a non-uniform and varying rate, and therefore exhibits substantially the same dose-dispensing rate over time.

Another object of the invention is to provide a dosage form that delivers a predetermined and prescribed dose in the same manner over time, while simultaneously lessening the amount retained or the residual drug left in and not delivered from the dosage form.

Another object of the invention is to provide a drug composition of matter comprising drug particles of 5 to 150 $\mu$m (microns) and hydrophilic polymer particles of 5 to 250 $\mu$m, characterized by the drug particles and the hydrophilic polymer particles functioning together to provide a uniform and nonvarying rate of release of both, which is free of a deviation and free of a decrease in the rate of the release over time.

Another object of the invention is to provide a dosage form comprising a membrane that surrounds a drug core comprising drug particles of 1 to 150 $\mu$m and hydrophilic polymer particles of 1 to 250 $\mu$m, which are codelivered from the dosage form through an exit formed by a process selected from the group consisting of a drilled exit, a bioerosion exit, a leaching exit, a solubilizing exit and an exit formed by rupture.

Another object of the invention is to provide a dosage form comprising a membrane comprising a semipermeable composition that surrounds a core comprising a drug layer comprising drug particles of 1 to 150 $\mu$m and polymer particles of 1 to 250 $\mu$m, and a displacement layer comprising an osmopolymer hydrogel that imbibes fluid, hydrates and increases in swelling volume, thereby displacing the drug layer through an exit selected from the group consisting of an orifice, a passageway, a pore, a microporous channel, a porous overlay, a porous insert, a micropore, a microporous membrane and a porepassageway.

Another object of the invention is to make available a process for providing a uniform and nonvarying drug delivery program from a dosage form, wherein the process comprises the steps of selecting drug particles of 1 to 150 $\mu$m; selecting hydrophilic polymer particles of 1 to 250 $\mu$m; blending the selected particles into a drug-polymer core; and surrounding the core with a membrane comprising means for delivering the drug from the core in a uniform and nonvarying rate of release over a period of time up to 30 hours.

Another object of the invention is to provide a dosage form for delivering a drug to human, wherein the dosage form comprises a drug composition comprising 0.05 ng to 1.2 g of drug having a particle size of 1 to 150 $\mu$m, and a hydrophilic polymer having a particle size of 1 to 250 $\mu$m; a push composition that imbibes fluid and expands for pushing the drug composition from the dosage form; a wall that surrounds the drug and the push composition that is permeable to the passage of fluid; an inner coat that surrounds the drug and push compositions, positioned between the inside surface of the wall and the drug and push compositions, for governing fluid imbibition into the drug and push compositions for 30 minutes to 4 hours and 30 minutes; and at least one exit means in the wall for delivering the drug composition at a uniform and nonvarying rate over time.

Other objects, features and advantages of the invention will be more apparent to those versed in the dispensing art, comprising medicine and pharmacy, from the following detailed specification taken in conjunction with the accompanying claims.

DESCRIPTION OF THE INVENTION

The following examples are illustrative of the invention, and should not be considered as limiting the invention in any way, as these examples and other equivalents thereof will become apparent to those versed in the dispensing art in the light of the present specification and the accompanying claims.

EXAMPLE 1

A dosage form for delivering a drug orally to the gastrointestinal tract of the drug-receiving patient in need of the drug's therapy is prepared as follows: first, 5 mg of 135 μm amlodipine besylate, a calcium channel blocker, is blended with a 5% solution of poly(vinylpyrrolidone) of 30,000 number-average molecular weight (available from General Aniline and Film Corporation, New York, N.Y.) in a fluid bed processor. Then, the granulated product is combined with 7.5 mg of 235 μm particle sized a poly(ethylene oxide) of 175,000 number-average molecular weight (available from Union Carbide Corporation, Danbury, Conn.), 0.5 mg of sodium chloride and 0.02 mg of stearic acid, and blended at 35 rpm for 7 minutes to provide a homogenous blend. The homogenous blend is compressed into a drug composition and surrounded with a wall comprising a semipermeable composition and an exit-forming agent.

The wall composition comprises 65 wt % cellulose acetate having an acetyl content of 34% and a 30,000 number-average molecular weight dissolved in acetone:water, to which 1.8 wt % triacetin and 1.5 wt % sodium chloride are added, stirring constantly. The drug composition is sprayed in a fluidized bed air-suspension coater to provide 10% wt wall. The dosage form is dried at 25° C. for 18 hours. The dosage form releases the amlodipine besylate in a nonvarying rate through microchannels formed by fluid leaching of the sodium chloride in the gastrointestinal fluid of the patient.

EXAMPLE 2

The procedure of the above example is followed in this example, wherein in the present example the drug is selected from the group consisting of 5 mg of lisinopril, indicated as an angiotensin converting enzyme inhibitor; 10 mg of buspirone hydrochloride, indicated as an antianxiety drug; and 5 mg of oxybutynin hydrochloride, indicated for relief of bladder instability; and wherein the lubricant is magnesium stearate and the semipermeable wall comprises mannitol.

EXAMPLE 3

A dosage form for the osmotically and hydrokinetically controlled release of a beneficial drug is made as follows: first, 500 mg of the oral antibacterial ciprofloxacin hydrochloride of 125 microparticle size is added to a mixing bowl, followed by the addition of 105 mg of sodium carboxymethylcellulose of 22,000 number-average molecular weight and 135 μm size. The ingredients are mixed for 3 to 5 minutes to yield a homogenous mix. Next, 10 mg of 88 microcrystalline cellulose of 11,000 number-average molecular weight and 0.05 mg of drug-delivery surfactant sodium lauryl sulfate are added to the bowl, and all the ingredients mixed for 5 minutes. Then, an aqueous solution containing 7.5 mg of poly(vinylpyrrolidone) of 30,000 number-average molecular weight is added, with mixing, and the resulting mixture is passed through an extruder onto a small tray and dried overnight. The granulation is dried for 5 hours at 50° C., and 0.03 mg of lubricant is added with mixing for 1 minute. A solid, fluid-imbibing osmotic core is prepared in a tablet press with a concave punch.

Next, an internal, drug-free subcoat is prepared comprising 94 wt % hydroxyethylcellulose of 90,000 number-average molecular weight; 6 wt % polyethylene glycol in distilled water is coated around the drug composition, and the subcoated drug composition is dried for 1 hour at 45° C. Then, an outer coat comprising a semipermeable composition and a pore-passageway former is prepared by adding cellulose acetate of 39.43% acetyl content to a cosolvent of methylene chloride and methanol to yield a solution effected by stirring and warming. Next, the pore former, sorbitol, is added to a cosolvent of water and methanol with mixing, followed by adding polyethylene glycol to produce the outer coating solution. Finally, the outer coating solution is coated around the subcoat in a pan coater and then dried for 18 hours at 45° C. in a forced-air oven to yield the desired dosage form. The dosage form, in operation in the gastrointestinal fluid of a human in need of drug therapy, provides a uniform and nonvarying order of drug release through exit passageways of controlled porosity, effected by the fluidic leaching of the soluble pore-forming additive incorporated in the semipermeable outer coat. The cooperation of the drug particles and the hydrophilic polymer particles provides a viscous gel that pushes the drug through the exits at the given rate.

EXAMPLE 4

The procedure of the above example is followed, with the provision that in this example the therapeutic member is selected from the group consisting of 40 mg of simvastatin for lowering cholesterol; 75 mg of venlafaxine antidepressant; 20 mg of fluoxetine antidepressant; 20 mg of antianginal nifedipine; 40 mg of lovastatin, indicated for lowering cholesterol; 20 mg of enalapril maleate, an angiotensin converting enzyme inhibitor; 120 mg of diltiazem for managing calcium ion influx; 500 mg of ciprofloxacin hydrochloride, an antibacterial; 100 mg of sertraline hydrochloride, an oral antidepressant; 100 mg of cyclosporin, an immunosuppressant; 1 mg of terazosin hydrochloride, an alpha adrenoceptor blocker; 50 mg of sumatriptan succinate, a 5-hydroxytryptamine receptor agonist; 40 mg of pravastatin sodium, a hypolipidemic; 500 mg of an anti-HIV proteinase inhibitor, such as nelfinavir, saquinavir, indinavir or ritonavir; an anti-HIV, such as zidovudine, didanosine or lamivudine; a reverse transcriptase inhibitor, such as loviride; an antiviral herpes, such as famciclovir or ganciclovir; 10 mg of alendronate sodium for treating osteoporosis; and 2.5 mg of conjugated estrogen, indicated for the treatment of vasomotor symptoms associated with menopause, atrophic vaginitis and osteoporosis loss of bone mass.

EXAMPLE 5

A dosage form for the oral uniform and nonvarying release of a drug to a biological drug receptor is manufactured as follows: first, 6000 g of verapamil hydrochloride, indicated for the treatment of angina and high blood pressure, having non-uniform particle size distribution between 1 to 900 μm, 3047 g of poly(ethylene oxide) having a number-average molecular weight of 300,000 and having 25% particles greater than 250 μm, 500 g of sodium chloride and 100 g of poly(vinylpyrrolidone) having a number-average molecular weight of 40,000 are added to the bowl of a Freund Flo-Coater®, a fluid bed granulator. The bowl is attached to the Flo-Coater and the granulation process is initiated. Next, the dry powders are air suspended and mixed for 5 minutes. Then, a solution prepared by dissolving 300 g of poly(vinylpyrrolidone) having a number-average molecular weight of 40,000 in 4,500 g of water is sprayed from two nozzles onto the powder. The coating conditions are monitored during the poly(vinylpyrrolidone) solution spraying as follows: a total spray rate of 240 g/min from each nozzle, an inlet temperature of 45° C., and an airflow of 1000 cfm. The coating process is computerized and automated in cycles. Each cycle contains 30 seconds of solution spraying, followed by 2 seconds of drying and 10 seconds of shaking of filter bags to unglue any possible powder deposits. At the end of the solution spraying period, the coated, granulated particles are continued in the drying process for 25 minutes. The machine is then turned off, and the coated granules are removed from the coater. The coated granules are sized using a fluid air mill. The granulation is transferred to a mixer, mixed and lubricated with 50 g of magnesium stearate, and then mixed with 4 g of butylated hydroxytoluene to provide the drug composition.

Next, a push-displacement composition is prepared as follows: first, 7342 g of poly(ethylene oxide) possessing a number-average molecular weight of 7 million, 2,000 g of sodium chloride, 200 g of hydroxypropyl methylcellulose of 11,200 number-average molecular weight, and 100 g of black ferric oxide are added to the Freund Flo-Coater's bowl. The bowl is attached to the Flo-Coater and the granulation process is started to mix the ingredients. The dry powders are air suspended and mixed for 6 minutes. Then, a solution prepared by dissolving 300 g of hydroxypropyl methylcellulose having a number-average molecular weight of 11,200 in 4,500 g of water is then sprayed from two nozzles onto the air-suspended powder mix. The coating conditions are monitored during the spraying of the hydroxypropyl methylcellulose solution. The conditions are identical to those described in the above drug granulation process, except that the drying cycle is less than 25 minutes. The granulated powders are removed from the granulator and sized in a fluid air mill. The granulation is transferred to a blender and mixed and lubricated with 50 g of magnesium stearate and 8 grams of butylated hydroxytoluene to yield the push-displacement composition.

Next, the drug composition and the push composition are compressed into a bilayered core. First, 300 mg of the drug composition comprising 180 mg of verapamil hydrochloride is added to the punch and tamped, then 100 mg of the push-displacement composition is added to the punch and the layers pressed under a pressure of 2,200 lb. into a 13/32 inch (1.032 cm) diameter, contacting bilayered arrangement.

Next, the bilayered core is coated with a subcoat. The subcoat comprises 95% hydroxyethylcellulose of 90,000 number-average molecular weight and 5% polyethylene glycol of 3,350 average-molecular weight. The ingredients are dissolved in water to make a 5% solid solution. The subcoat-forming composition is sprayed onto and around the bilayer core in a 24-inch Vector Hi-Coater°. The dry subcoat weighs 79 mg.

Next, the hydroxyethylcellulose, a hydroxyalkylcellulose, subcoated bilayered cores are over coated with a semipermeable composition. The membrane-forming overcoat composition comprises 60% cellulose acetate having an acetyl content of 39.8%, 35% hydroxypropyl cellulose of 40,000 number-average molecular weight and 5% polyethylene glycol of 3,350 average-molecular weight dissolved in methylene chloride:methanol (90:10 wt:wt) cosolvent to make a 4% solid solution. The semipermeable membrane-forming composition is sprayed onto and around the sub-coated bilayer core. The semipermeable membrane, after drying, weighs 43 mg.

Next, two 27 mil (0.686 mm) exit passageways are drilled through the outer semipermeable membrane and the inner subcoat to connect the drug layer with the exterior of the dosage form. The residual solvents are removed by drying for 96 hours at 50° C. and 50% humidity. Finally, the dosage forms are dried for 2 hours at 50° C. to remove any excess moisture.

The dosage form manufactured by this procedure comprises a drug composition with a weight of 300 mg, consisting of 180 mg of verapamil hydrochloride, 91.41 mg of poly(ethylene oxide) of 300,000 molecular weight, mg of poly(vinylpyrrolidone) of 40,000 molecular weight, 15 mg of sodium chloride, 0.12 mg of butylated hydroxytoluene and 1.5 mg of magnesium stearate. A push-displacement composition that weighs 100 mg consisting of 73.5 mg of poly(ethylene oxide) of 7,000,000 molecular weight, 20 mg of sodium chloride, 5 mg of hydroxypropyl methylcellulose of 11,200 molecular weight, 0.92 mg of black ferric oxide, 0.08 mg of butylated hydroxytoluene and 0.5 mg of magnesium stearate. The dosage form subcoat weighs 78.8 mg, and consists of 74.86 mg of hydroxyethylcellulose of 90,000 molecular weight and 3.94 mg of polyethylene glycol of 3,350 molecular weight. The outer wall weighs 42.6 mg, and consists of 25.56 mg of cellulose acetate of 39.8% acetyl content, 14.90 mg of hydroxypropyl cellulose of 40,000 molecular weight, and 2.13 mg of polyethylene glycol of 3,350 molecular weight. This dosage form has a $(dm/dt)_t$ mean release rate of 18.6 mg/hr between the fourth and ninth hours.

Figure 1:
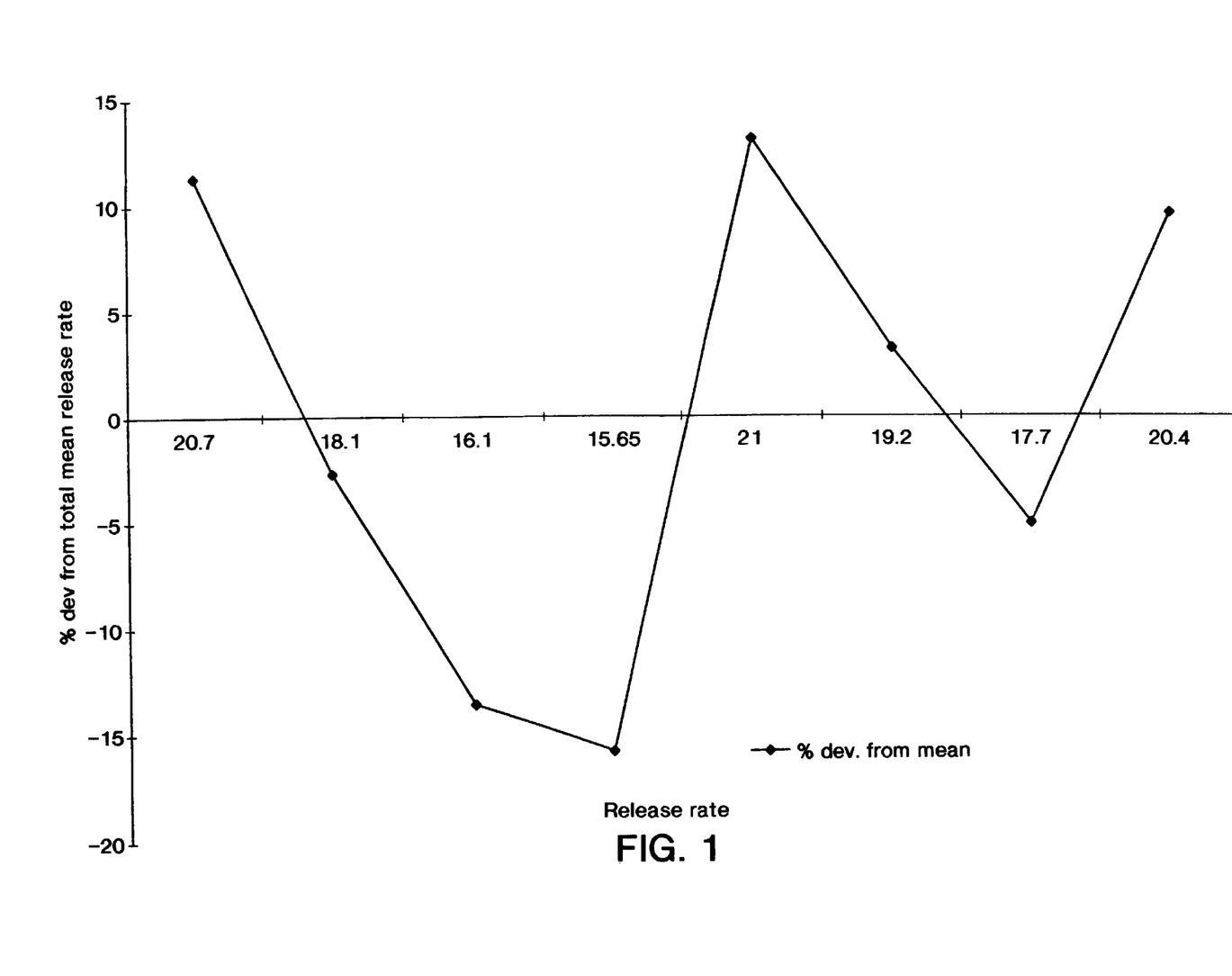
FIG. 1 illustrates the drug release rate variation with a drug possessing a particle size of 2 to 900 $\mu$m in the presence of a polymer possessing 25% and more of particles of greater than 250 $\mu$m size.

The delivery pattern for the dosage form prepared by this example is illustrated in FIG. 1. In FIG. 1, the non-uniform variability release rate is seen over the steady portion illustrated by the line starting at zero and extending to the right of the figure. The release rate variation is for a drug having a 1 to 900 μm particle size released in the presence of a hydrophilic polymer having greater than 25% particles larger than 250 μm. The solid line depicts the percent deviation from the total mean release rate. The mean release rate for a given dosage form is expressed by the number along the line starting at zero. In FIG. 1, erratic behavior is seen because the dosage form lacks uniform particles of a limited range. The erratic behavior is characterized by a substantial deviation of individual systems from the mean (dosage form) steady state release rate performance. This erratic behavior phenomena is attributed to the inability of the hydrophilic polymer, the poly(ethylene oxide), to carry and suspend large drug particles, the verapamil hydrochloride; the difference in the hydration time between the large and small drug particles; and the larger hydrophilic polymer particles greater than 250 μm, which significantly changes the hydration and the drug suspending properties of the drug compositional layer that resulted in a large percent negative deviation in the $(dm/dt)_i$ from the $(dm/dt)_t$. The expression $(dm/dt)t$ denotes the total mean release rate for all dosage forms in the zero portion, $(dm/dt)_i$ denotes the mean release rate of an individual dosage form in four to nine hours, and $(\% \text{ dev})_i$ denotes the percent deviation in an individual dosage form mean release rate (four to nine hours) from the total mean release rate. The figure reports results obtained from the following equation:

$$(\% \ dev) = \frac{(dm/dt)_j - (dm/dt)_t}{(dm/dt)_t}$$

EXAMPLE 6

A dosage form for the delivery of a drug orally to a human is prepared as follows: first 6000 g of verapamil hydrochloride having a particle size of less than 150 μm, 3047 g of poly(ethylene oxide) possessing a number-average molecular weight of 300,000 with 25% particles larger than 250 μm, 500 g of sodium chloride, and 100 g of poly (vinylpyrrolidone) having a number-average molecular weight of 40,000 are added to the bowl of a fluid bed granulator. The granulation is carried out for seven to ten minutes. Next, the dry powders are air suspended and mixed for five minutes. Then, a solution prepared by dissolving 300 g of poly(vinylpyrrolidone) of 40,000 number-average weight in 4,500 g of distilled water is sprayed from two nozzles onto the dry powder. The coating conditions are monitored during spraying as follows: a total spray rate of 240 g/min from each nozzle, an inlet temperature of 45° C. and a process air flow of 1000 cfm. The coating process is automated in cycles. Each cycle consist of 30 seconds of solution spraying, followed by 2 seconds of drying and 10 seconds of shaking of filter bags to unglue any possible powder deposits. At the end of the solution spraying time, the coated granulated particles are continued with the drying process for 25 minutes. The machine is then turned off, and the coated granules are removed from the coater. The coated granules are sized using a fluid air mill, and then the granulation is transferred to a mixer, mixed and lubricated with 50 g of magnesium stearate, and mixed with 4 g of butylated hydroxytoluene to provide the drug composition used for forming a layer in the bilayer core.

Next, a push composition is prepared as follows: first, 7,342 g of poly(ethylene oxide) of 7 million number-average molecular weight, 2,000 g of sodium chloride, 200 g of hydroxypropyl methylcellulose of 11,200 number-average molecular weight, and 100 g of black ferric oxide are added to the bowl of a fluid bed granulator. The granulation process is started and the dry powders are air suspended and mixed for 6 minutes. Then, a solution is prepared by dissolving 300 g of hydroxypropyl methylcellulose possessing a 11,200 number-average molecular weight in 4,500 g of water and sprayed onto the air-suspended powder mix. The coating conditions are monitored during the spraying and the physical conditions are identical to those described for the above drug granulation, except that the drying cycle is less than 25 minutes. The granulated powders are then removed from the granulator. The granules are sized in a fluid air mill, then transferred to a blender and lubricated while mixing with 50 g of magnesium stearate and 8 g of butylated hydroxytoluene to yield the push composition.

Next, the drug composition and the push composition are pressed into a bilayered core with the layers in contacting arrangement. First, 400 mg of the drug composition comprising 240 mg of verapamil hydrochloride is added to a tablet punch and tamped, then 135 mg of the push composition is added to the punch and the layers are pressed under a pressure head of 2,300 lb. in a 7/16 inch (1.11 cm) diameter, contacting bilayered arrangement. The bilayered-core tablets are coated with a subcoat. The subcoat comprises 95% (hydroxyethylcellulose) of 90,000 molecular weight and 5% polyethylene glycol of 3,350 molecular weight, dissolved in water to provide a 5% solid solution. The subcoat-forming composition is sprayed onto and around the bilayered core in a coater. The dry subcoat weighs 93 mg.

Next, an outer coat is applied to the dosage form. The subcoated bilayered-core tablets are coated with a semipermeable membrane wall. The membrane-forming composition comprises 60% cellulose acetate having a 39.8% acetyl content, 35% hydroxypropyl cellulose of 40,000 molecular weight and 5% polyethylene glycol of 3,350 molecular weight. The wall-forming composition is dissolved in methylene chloride:methanol (90:10 wt:wt) cosolvent to make a 4% solid solution. The semipermeable membrane wall-forming composition is sprayed onto and around the subcoated bilayer core in a coater to provide a two-coated dosage form. The semipermeable membrane, dry, weighs 51 mg.

Next, two 27 mil (0.686 mm) exit passageways are drilled through the outer and inner coats to connect the drug layer with the exterior of the dosage form. The residual solvents are removed by drying for 96 hours at 50° C. and 50% humidity. Then, the osmotic dosage forms are dried for 2 hours at 50° C. to remove excess moisture.

The dosage form manufactured by this procedure comprises a drug composition with a weight of 400 mg, consisting of 240 mg of verapamil hydrochloride, 121.88 mg of polyethylene oxide of 300,000 molecular weight, 16 mg of poly(vinylpyrrolidone) of 40,000 molecular weight, 20 mg of sodium chloride, 2 mg of magnesium stearate and 0.16 mg of butylated hydroxytoluene. The push composition of the dosage form weighs 135 mg and consists of 99.23 mg of poly(alkylene oxide), poly(ethylene oxide) of 7 million molecular weight, 27 mg of sodium chloride, 6.75 mg of hydroxypropyl methylcellulose of 11,200 molecular weight, 1.24 mg of ferric oxide, 0.675 mg of magnesium stearate and 0.108 mg of butylated hydroxytoluene. The inner subcoat weighs 93.1 mg and consists of 88.45 mg of hydroxyethylcellulose of 90,000 molecular weight and 46.55 mg of polyethylene glycol of 3,350 molecular weight. The outer coat weighs 51.1 mg and consists of 30.66 mg of cellulose acetate of 39.8% acetyl content, 17.89 mg of hydroxypropyl cellulose of 40,000 molecular weight and 2.57 mg of polyethylene glycol of 3,350 molecular weight. The dosage form prepared by this example has a $(dm/dt)_t$ mean release rate of 27 mg/hr during hours 4 to 9.

Figure 2:
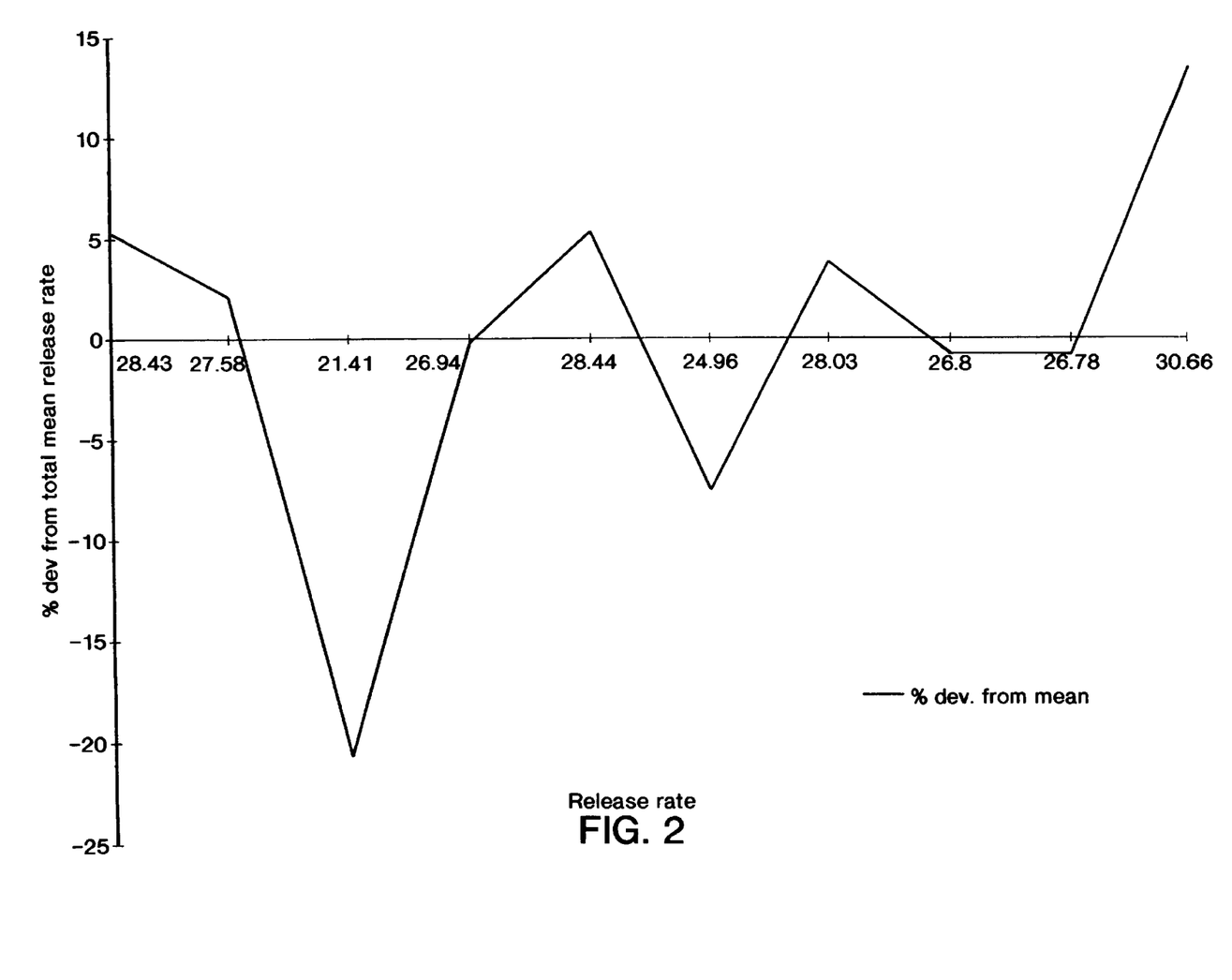
FIG. 2 illustrates the drug release rate variation from a dosage form with a drug size of less than 150 $\mu$m in the presence of a polymer possessing 25% and more of particles of greater than 250 μm size.

The drug delivery pattern for the dosage form prepared by this invention is seen in drawing FIG. 2. In FIG. 2, the nonuniform variability is depicted for the dosage form. The erratic release behavior is characterized by a substantial and pronounced deviation of individual dosage forms from the mean dosage form steady-state rate performance. The figure denotes that larger polymer particles of from 250 μm significantly change the hydration, drug carrying ability and suspension properties of the drug composition. This results in a large percent negative deviation in the expression $(dm/dt)_i$ from the expression $(dm/dt)_t$.

EXAMPLE 7

A dosage form for the oral delivery of a drug to the gastrointestinal tract of a human in need of drug therapy is prepared as follows: first, 6000 g of verapamil hydrochloride having a particle size of 150 μm or smaller, 3047 g of poly(ethylene oxide) of 300,000 molecular weight having a particle size of 250 μm or smaller, 500 g of powdered sodium chloride, and 100 g of poly(vinylpyrrolidone) having a 40,000 molecular weight are added to a coater and granulated in air for 5 minutes. Next, a solution is prepared by dissolving 300 g of poly(vinylpyrrolidone) of 40,000 molecular weight in 4,500 g of water and sprayed onto the powder. The spray rate is 240 g/min at an inlet temperature of 45° C. and an air flow of 1000 cfm. The spraying is effected in two cycles consisting of 30 seconds of solution spraying, followed by 2 seconds of drying and 10 seconds of shaking to unglue powder deposits. At the end of the solution spraying period, the coated, granulated particles are dried for an additional 25 minutes. Then, the coated granules are sized in a fluid air mill. The granulation is transferred to a mixer and lubricated with 50 g of magnesium stearate and 4 g of butylated hydroxytoluene to yield the drug composition.

Next, a push-displacement composition is prepared as follows: first, 7,342g of poly(ethylene oxide) of 7 million molecular weight, 2,000 g of sodium chloride, 2,000 g of hydroxypropyl methylcellulose of 11,200 molecular weight, and 100 g of black ferric oxide are added to the bowl of a fluid bed granulator. The granulation is started and the powders mixed for 6 minutes. Then, a solution is prepared by dissolving 300 g of hydroxypropyl methylcellulose of 11,200 molecular weight in water and sprayed onto the air-suspended particles. The coating process is as described above. The granules are sized in a fluid air mill and transferred to a blender, and blended with 50 g of magnesium stearate and 8 g of butylated hydroxytoluene to yield the push-displacement composition.

Next, the drug composition and the push composition are compressed into a bilayered tablet as follows: first, 400 mg of the drug composition containing 240 mg of verapamil hydrochloride is added to the die and tamped, then it is overlaid with 135 mg of the push composition and the two compositions pressed under 2,300 lb. into a 7/16 inch (1.11 cm) diameter, contacting, bilayered arrangement.

Next, the compressed bilayer tablets are coated with a subcoat laminate. The subcoat comprises 95% hydroxyethylcellulose of 90,000 molecular weight and 5% polyethylene glycol of 3,350 molecular weight dissolved in distilled water to make a solid solution. The subcoat-forming composition is sprayed onto and around the bilayered tablet in a coater to provide an encompassing laminate. The dry subcoat weighs 93 mg.

Next, the subcoat is overcoated with a semipermeable wall. The semipermeable composition comprises 60% cellulose acetate having an acetyl content of 39.8%, 35% hydroxypropyl cellulose of 40,000 molecular weight and 5% polyethylene glycol of 3,350 average-molecular weight. The wall-forming composition is dissolved in a methylenechloride:methanol (90:10 wt:wt) cosolvent to make a 4% solid solution. The semipermeable overcoat is sprayed onto and around the subcoat. The semipermeable wall weighs 51 mg.

Next, two 27 mil (0.686 mm) exit passageways are drilled through the dual coats to connect the drug layer with the exterior of the dosage form. The residual solvents are removed by drying for 96 hours at 50° C. and 50% humidity. Next, the osmotic, fluid-imbibing dosage forms are dried for 2 hours at 50° C. to remove excess moisture.

Figure 3:
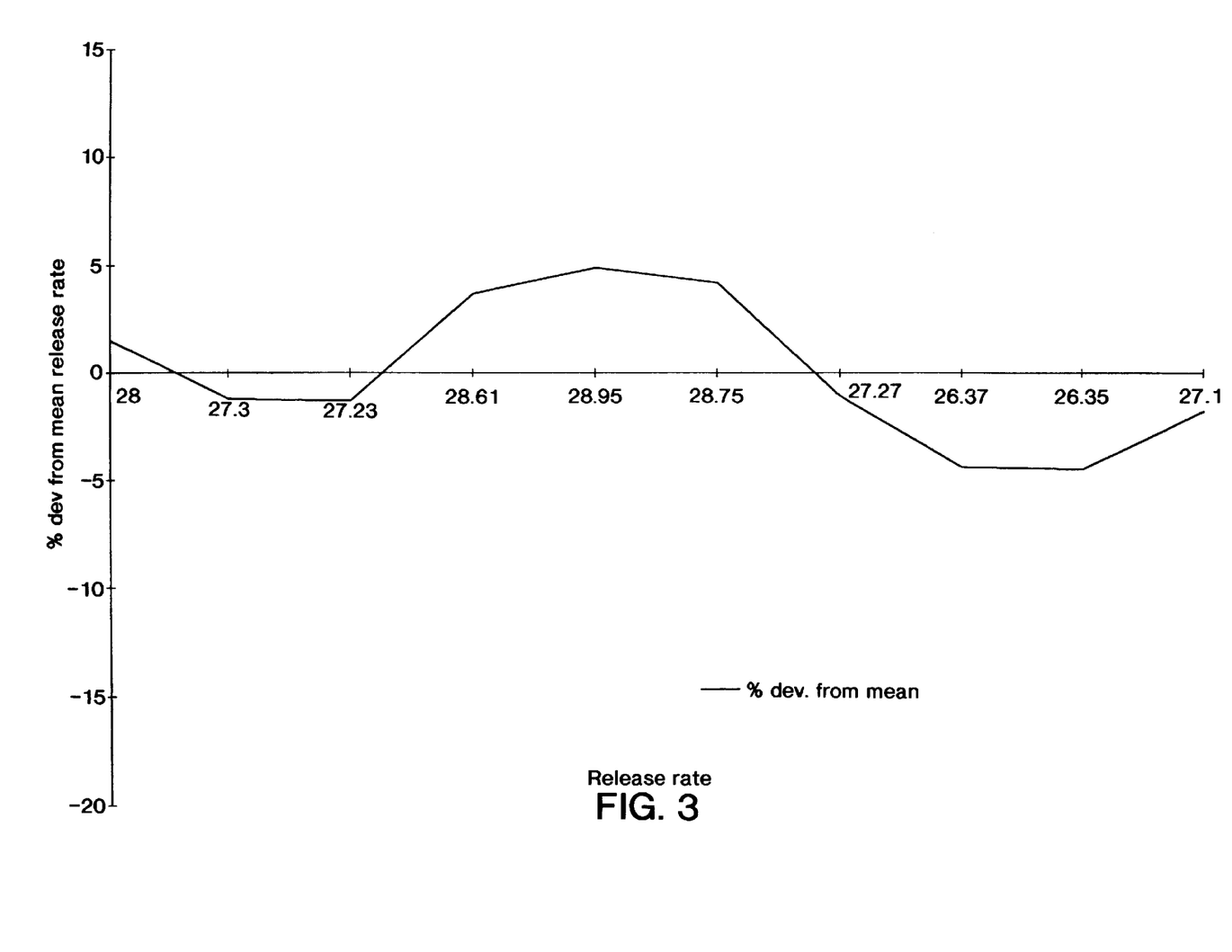
FIG. 3 illustrates the pronounced decrease in the variation of the drug release rate when the dosage form comprises a drug size of less than 150 μm accompanied by a polymer size of less than 250 μm.

The dosage form prepared by this example embraces the same composition as the example immediately above, except for the controlled drug particle size and the controlled hydrophilic polymer particle size in the drug composition. This double particle control produces uniform dose dispensing, free of a wide variation in the dose dispensing pattern. Accompanying FIG. 3 depicts the drug delivery pattern for this example. The figure depicts a release rate of $(dm/dt)_t$ equal to 27.9 mg/hr during hours 4 to 9. The figure illustrates that a nonuniform variability is not observed for the dosage form provided by this example.

EXAMPLE 8

A dosage form prepared according to Example 7, wherein the drug in the dosage form is a calcium channel blocking drug selected from the group consisting of isradipine, nilvadipine, flunarizine, nimodipine, diltiazem, nicardipine, nitrendipine, nisoldipine, felodipine, amlodipine, cinnarizine and fendiline.

EXAMPLE 9

The procedure described in the above example is repeated in this example, with the processing conditions as set forth previously, except that in this example the drug is an angiotensin converting enzyme inhibitor selected from the group consisting of alacepril, benazepril, cilazapril, captopril, delapril, enalapril, fosinopril, lisinopril, moveltipril, perindopril, quinapril, ramipril, spirapril and zofenopril.

EXAMPLE 10

The procedures of the above examples are followed in this example, with the addition of the drug, which is protected against oxidative attack and oxidation by adding to the processing drug composition 0.05 ng to 7 mg of an antioxidant selected from the group consisting of d-alpha tocopherol, dl-alpha tocopherol, d-alpha tocopherol acetate, d-alpha tocopherol acid succinate, dl-alpha tocopherol acid succinate, dl-alpha tocopherol palmitate, ascorbic acid, ascorbyl oleate, ascorbyl palmitate, butylated hydroxyanisole, butylated hydroxytoluene, sodium ascorbate, calcium ascorbate and propyl gallate stabilizers.

EXAMPLE 11

The procedures of the above examples are followed in this example with an addition to the drug composition comprising 0.05 ng to 7 mg of an antioxidant stabilizer and 0.05 ng to 7.5 mg of a lubricant selected from the group consisting of magnesium stearate, calcium stearate, magnesium oleate, magnesium palmitate, corn starch, potato starch, bentonite, citrus pulp and stearic acid; and with all the ingredients in the drug composition, when expressed in weight percent, equal to 100 wt %.

EXAMPLE 12

The procedures of the above examples are followed in this example with an addition to the drug composition of means protecting the drug against daylight and ultraviolet light, wherein the addition comprises adding to the drug composition 0.01 to 10 mg of surface-active agent selected from anionic, cationic, amphoteric and nonionic surfactants, including dialkyl sodium sulfosuccinate, polyoxyethylene glycerol, polyoxyethylene stearyl ether, propoxy-ethoxy copolymer, polyoxyethylene fatty alcohol ester, polyoxyethylene fatty acid ester, ethoxylated hydrogenated castor oil and butoxylated hydrogenated castor oil; and adding to the drug composition 0.01 to 10 mg of riboflavin to stabilize the drug against light.

ADDITIONAL DISCLOSURE OF THE INVENTION

In the specification and accompanying claims, the term "beneficial agent" includes drugs. The term "drug" includes any physiologically or pharmacologically active substance that produces a local or a systemic effect in animals, including warm-blooded mammals, humans and primates; avians, household, sport, and farm animals; laboratory animals; fishes; reptiles and zoo animals. The term "physiologically" as used herein generically denotes the administration of a drug to produce generally normal drug levels and functions. The term "pharmacologically" generally denotes variations in response to the amount of drug administered to a host. The drug can be in various forms, such as unchanged molecules, molecular complexes, pharmacologically acceptable salts, such as hydrochloride, hydrobromide, sulfate, laurate, palmitate, phosphate, nitrite, nitrate, borate, acetate, maleate, tartrate, oleate, salicylate, and the like. For acidic drugs, salts of metals, amines or organic cations, for example, quaternary ammonium, can be used. Derivatives of drugs, such as bases, esters and amides can be used. A drug that is water insoluble can be used in a form that is a water soluble derivative thereof, or as a base derivative thereof, which in either instance, or by its delivery by the osmotic system, is converted by enzymes, hydrolyzed by the body pH, or by other metabolic processes to the original therapeutically active form. The amount of drug in a dosage form, that is, in the drug composition, is 25 ng to 750 mg. The dosage form comprising the drug can be administered one to three times a day.

The active drug that can be delivered includes inorganic and organic compounds without limitation, including drugs that act on the peripheral nerves, adrenergic receptors, cholinergic receptors, nervous system, skeletal muscles, cardiovascular system, smooth muscles, blood circulatory system, synoptic sites, neuroeffector junctional sites, endocrine system, hormone systems, immunological system, organ systems, reproductive system, skeletal system, autocoid systems, alimentary and excretory systems, inhibitory of autocoids and histamine systems and physiological systems. The active drug that can be delivered for acting on these animal systems includes depressants, beta-blockers, hypnotics, sedatives, psychic energizers, tranquilizers, anticonvulsants, muscle relaxants, steroids, antiparkinson agents, analgesics, anti-inflammatories, polypeptides, local anesthetics, muscle contractants, antimicrobials, antimalarials, hormonal agents, contraceptives, sympathomimetics, diuretics, antiparasitics, neoplastics, hypoglycemics, ophthalmics, electrolytes, diagnostic agents, cardiovascular drugs, calcium channel blockers, angiotensin converting enzyme inhibitors, and the like.

Exemplary of drugs that can be delivered from the dosage form of this invention include a drug selected from the group consisting of amifostine, prochlorperazine edisylate, ferrous sulfate, aminocaproic acid, potassium chloride, mecamylamine hydrochloride, procainamide hydrochloride, amphetamine sulfate, benzphetamine hydrochloride, isoproterenol sulfate, methamphetamine hydrochloride, phenmetrazine hydrochloride, bethanechol chloride, methacholine chloride, pilocarpine hydrochloride, antropine sulfate, methscopolamine bromide, isopropamide iodide, tridihexethyl chloride, phenformin hydrochloride, methylphenidate hydrochloride, oxprenolol hydrochloride, metoprolol tartrate, cimetidine hydrochloride, diphenidol, meclizine hydrochloride, prochlorperazine maleate, phenoxybenzamine, thiethylperazine, maleate, anisindione, diphenadione erythrityl tetranitrate, isoflurophate, reserpine, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, estrogenic progestational, corticosteroids, hydrocortisone acetate, cortisone acetate, triamcinolone, methyltestosterone, 17β-estradiol, ethinyl estradiol, ethinyl estradiol 3-methyl ether, prednisolone, 17-hydroxyprogesterone acetate, 19-norprogesterone, norgestrel, norethindrone, norethisterone, progesterone, norgesterone, norethyndral, aspirin, indomethacin, aproxen, fenoprofen, sulindac, diclofenac, indoprofen, nitroglycerin, propranolol, metoprolol, valproate, oxprenolol, timolol, atenolol, alprenolol, cimetidine, clonidine, imipramine, levodopa, chlorpromazine, methyldopa, dihydroxyphenylalanine, pivaloyloxyethyl ester of ε-methyldopa hydrochloride, theophylline, calcium gluconate ferrous lactate, ketoprofen, ibuprofen, cephalexin, erythromycin, haloperidol, zomepirac, vincamine, diazepam, phenoxybenzamine, β-blocking agents; calcium-channel blocking drugs, such as nifedipine, diltiazem, isradipine, nilvadipine, verapamil, flunarizine, nimodipine, felodipine, amlodipine, cinnarizine and fendiline; angiotensin converting enzyme inhibitors selected from the group consisting of angiotensin converting enzyme inhibitors that are essentially free of sulfur, angiotensin converting enzyme inhibitors containing a sulfhydryl group, angiotensin converting enzyme inhibitors containing a linear sulfide, angiotensin converting enzyme inhibitors containing a cyclic sulfide, angiotensin converting enzyme inhibitors containing a methylsulfonal group, and angiotensin enzyme inhibitors represented by a member selected from the group consisting of ramipril, fosinopril, benazepril, libenzapril, alacepril, cilazapril, cilazaprilat, perindopril, zofenopril, enalapril, lisinopril, imidapril, spirapril, rentiapril, captopril, delapril,, indolapril and quinapril; propranolol, naproxen, phenylpropanolamine, glipizide, venlafaxine, and beneficial drugs known to the dispensing arts in *Pharmaceutical Sciences*, Remington, 18th Ed. (1990) Mack Publishing Co., Easton, Pa.; *Physicians' Desk Reference*, 50th Ed. (1996) Medical Economics Co., Montvale, N.J.; and *USP Dictionary* (1995) U.S. Pharmacopeial Convention, Inc., Rockville, Md.

The dosage form of the invention is provided with at least one exit means. The exit means cooperates with the drug core for the uniform and substantially nonvarying drug-dose release from the dosage form. The exit means can be provided during the manufacture of the dosage form or during drug delivery by the dosage form in a fluid environment of use. The expression "exit means" as used for the purpose of this invention includes a member selected from the group consisting of a passageway; an aperture; an orifice; a bore; a pore; a micropore; a porous element through which a drug can be pumped, diffuse, travel or migrate; a hollow fiber; a capillary tube; a porous insert; a porous overlay; a microporous member; and a porous composition. The expression also includes a compound or polymer that erodes, dissolves or is leached from the outer coat or wall or inner coat to form at least one exit, or a multiplicity of exits. The compound or polymer includes an erodible poly(glycolic) acid or poly(lactic) acid in the outer or inner coats; a gelatinous filament; a water-removable poly(vinyl alcohol); a leachable compound, such as a fluid removable pore-former selected from the group consisting of inorganic and organic salt, oxide and carbohydrate. An exit, or a plurality of exits, can be formed by leaching a member selected from the group consisting of sorbitol, lactose, fructose, glucose, mannose, galactose, talose, sodium chloride, potassium chloride, sodium citrate and mannitol to provide a uniform-release dimensioned pore-exit means. The exit means can have any shape, such as round, triangular, square, elliptical and the like for the uniform metered dose release of a drug from the dosage form. The dosage form can be constructed with one or more exits in spaced apart relation or one or more surfaces of the dosage form. The exit means can be performed by drilling, including mechanical and laser drilling, through the outer coat, the inner coat, or both. Exits and equipment for forming exits are disclosed in U.S. Pat. Nos. 3,845,770 and 3,916,899, by Theeuwes and Higuchi; in U.S. Pat. No. 4,063,064, by Saunders, et al.; and in U.S. Pat. No. 4,088,864, by Theeuwes, et al. Exit means comprising dimensions sized, shaped and adapted as a releasing pore formed by aqueous leaching to provide a drug releasing pore are disclosed in U.S. Pat. Nos. 4,200,098 and 4,285,987, by Ayer and Theeuwes.

The particles used for the purpose of this invention are produced by comminution that produces the size of the drug and the size of the accompanying hydrophilic polymer used according to the mode and the manner of the invention. The means for producing particles include spray drying, sieving, lyophilization, crushing, grinding, jet milling, micronizing and chopping to produce the intended micron particle size. The process can be performed by size reduction equipment, such as a micropulverizer mill, a fluid energy grinding mill, a grinding mill, a roller mill, a hammer mill, an attrition mill, a chaser mill, a ball mill, a vibrating ball mill, an impact pulverizer mill, a centrifugal pulverizer, a coarse crusher and a fine crusher. The size of the particle can be ascertained by screening, including a grizzly screen, a flat screen, a vibrating screen, a revolving screen, a shaking screen, an oscillating screen and a reciprocating screen. The processes and equipment for preparing particles are disclosed in *Pharmaceutical Sciences*, Remington, 17th Ed., pp. 1585–1594 (1985); *Chemical Engineers Handbook*, Perry, 6th Ed., pp. 21-13 to 21-19 (1984); *Journal of Pharmaceutical Sciences*, Parrot, Vol. 61, No. 6, pp. 813–829 (1974); and *Chemical Engineer*, Hixon, pp. 94–103 (1990).

In accordance with the practice of this invention, it has been found that the dosage form can be provided with a semipermeable wall, also identified for the purpose of this invention as an outercoat. The semipermeable wall is permeable to the passage of an external fluid, such as water and biological fluids, and it is substantially impermeable to the passage of a beneficial agent, osmagent, osmopolymer and the like. The selectively semipermeable compositions used for forming the wall are essentially nonerodible and they are insoluble in biological fluids during the life of the dosage form.

Representative polymers for forming the wall comprise semipermeable homopolymers, semipermeable copolymers, and the like. In one presently preferred embodiment the compositions comprise cellulose esters, cellulose ethers and cellulose ester-ethers. The cellulosic polymers have a degree of substitution (DS) of their anhydroglucose unit of from greater than 0 up to 3, inclusive. Degree of substitution (DS) means the average number of hydroxyl groups originally present on the anhydroglucose unit that are replaced by a substituting group or converted into another group. The anhydroglucose unit can be partially or completely substituted with groups such as acyl, alkanoyl, alkenoyl, aroyl, alkyl, alkoxy, halogen, carboalkyl, alkylcarbamate, alkylcarbonate, alkylsulfonate, alkysulfamate, semipermeable polymer forming groups, and the like.

The semipermeable compositions typically include a member selected from the group consisting of cellulose acylate, cellulose diacylate, cellulose triacylate, cellulose acetate, cellulose diacetate, cellulose triacetate, mono-, di- and tri-cellulose alkanylates, mono-, di-, and tri-alkenylates, mono-, di-, and tri-aroylates, and the like. Exemplary polymers include cellulose acetate having a DS of 1.8 to 2.3 and an acetyl content of 32 to 39.9%; cellulose diacetate having a DS of 1 to 2 and an acetyl content of 21 to 35%; cellulose triacetate having a DS of 2 to 3 and an acetyl content of 34 to 44.8%; and the like. More specific cellulosic polymers include cellulose propionate having a DS of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45%, and a hydroxyl content of 2.8 to 5.4%; cellulose acetate butyrate having a DS of 1.8, an acetyl content of 13 to 15%, and a butyryl content of 34 to 39%; cellulose acetate butyrate having an acetyl content of 2 to 29%, a butyryl content of 17 to 53%, and a hydroxyl content of 0.5 to 4.7%; cellulose triacylates having a DS of 2.6 to 3, such as cellulose trivalerate, cellulose trilamate, cellulose tripalmitate, cellulose trioctanote and cellulose tripropionate; cellulose diesters having a DS of 2.2 to 2.6, such as cellulose disuccinate, cellulose dipalmitate, cellulose dioctanoate, cellulose dicarpylate, and the like; and mixed cellulose esters, such as cellulose acetate valerate, cellulose acetate succinate, cellulose propionate succinate, cellulose acetate octanoate, cellulose valerate palmitate, cellulose acetate heptonate, and the like. Semipermeable polymers are known in U.S. Pat. No. 4,077,407, and they can be synthesized by procedures described in *Encyclopedia of Polymer Science and Technology*, Vol. 3, pp. 325–354 (1964), Interscience Publishers Inc., New York, N.Y.

Additional semipermeable polymers for forming the outer wall comprise cellulose acetaldehyde dimethyl acetate; cellulose acetate ethylcarbamate; cellulose acetate methyl carbamate; cellulose dimethylaminoacetate; semipermeable polyamide; semipermeable polyurethanes; semipermeable sulfonated polystyrenes; cross-linked selectively semipermeable polymers formed by the coprecipitation of an anion and a cation, as disclosed in U.S. Pat. Nos. 3,173,876; 3,276,586; 3,541,005; 3,541,006 and 3,546,142; semipermeable polymers, as disclosed by Loeb, et al. in U.S. Pat. No. 3,133,132; semipermeable polystyrene derivatives; semipermeable poly(sodium styrenesulfonate); semipermeable poly(vinylbenzyltremethylammonium chloride); and semipermeable polymers exhibiting a fluid permeability of $10^{-5}$ to $10^{-2}$ (cc. mil/cm hr.atm), expressed as per atmosphere of hydrostatic or osmotic pressure differences across a semipermeable wall. The polymers are known to the art in U.S. Pat. Nos. 3,845,770; 3,916,899 and 4,160,020; and in *Handbook of Common Polymers*, Scott and Roff (1971) CRC Press, Cleveland, Ohio.

The subcoat of the invention is in contacting position with the inner surface of the semipermeable wall, which outer semipermeable wall surrounds and encases the inner subcoat. The inner subcoat is 0.01 to 3 mm thick and it comprises a member selected from group consisting of hydroxyalkylcellulose, hydroxyethylcellulose, hydroxyisopropylcelluose, hydroxybutylcellulose and hydroxyphenylcellulose. The hydroxyalkylcellulose comprises a 9,500 to 1,250,000 number-average molecular weight.

The drug composition comprises a hydrophilic polymer for providing a hydrophilic polymer particle in the drug composition that contributes to the uniform and nonvarying drug delivery pattern. Representatives of these polymers comprise a member selected from the group consisting of a poly(alkylene oxide) of 100,000 to 750,000 number-average molecular weight, including poly(ethylene oxide), poly (methylene oxide), poly(butylene oxide) and poly(hexylene oxide); and a poly(carboxymethylcellulose) of 40,000 to 400,000 number-average molecular weight, represented by poly(alkali carboxymethylcellulose), poly(sodium carboxymethylcellulose), poly(potassium carboxymethylcellulose) and poly(lithium carboxymethylcellulose). The drug composition can comprise a hydroxypropylalkylcellulose of 9,200 to 125,000 number-average molecular weight for enhancing the delivery properties of the dosage form as represented by hydroxypropylethylcellulose, hydroxypropyl methylcellulose, hydroxypropylbutylcellulose and hydroxypropylpentylcellulose; and a poly(vinylpyrrolidone) of 7,000 to 75,000 number-average molecular weight for enhancing the flow properties of the dosage form.

The push-displacement composition in contacting layered arrangement comprises a polymer that imbibes an aqueous or biological fluid and swells to push the drug composition through the exit means from the dosage form. Representatives of fluid-imbibing displacement polymers comprise a member selected from the group consisting of a poly (alkylene oxide) of 1 million to 15 million number-average molecular weight, as represented by poly(ethylene oxide) and poly(alkali carboxymethylcellulose) of 500,000 to 3,500,000 number-average molecular weight, wherein the alkali is sodium, potassium or lithium. Examples of further polymers for the formulation of the push-displacement composition comprise osmopolymers comprising polymers that form hydrogels, such as Carbopol® acidic carboxypolymer, a polymer of acrylic cross-linked with a polyallyl sucrose, also known as carboxypolymethylene, and carboxyvinyl polymer having a molecular weight of 250,000 to 4,000,000; Cyanamer® polyacrylamides; cross-linked water swellable indenemaleic anhydride polymers; Good-rite® polyacrylic acid having a molecular weight of 80,000 to 200,000; Aqua-Keeps® acrylate polymer polysaccharides composed of condensed glucose units, such as diester cross-linked polygluran; and the like. Representative polymers that form hydrogels are known to the prior art in U.S. Pat. No. 3,865,108, issued to Hartop; U.S. Pat. No. 4,002,173, issued to Manning; U.S. Pat. No. 4,207,893, issued to Michaels; and in *Handbook of Common Polymers*, Scott and Roff, Chemical Rubber Co., Cleveland, Ohio.

The osmagent, also known as osmotic solute and osmotically effective agent, which exhibits an osmotic pressure gradient across the outer wall and subcoat, comprises a member selected from the group consisting of sodium chloride, potassium chloride, lithium chloride, magnesium sulfate, magnesium chloride, potassium sulfate, sodium sulfate, lithium sulfate, potassium acid phosphate, mannitol, urea, inositol, magnesium succinate, tartaric acid raffinose, sucrose, glucose, lactose, sorbitol, inorganic salts, organic salts and carbohydrates.

Exemplary solvents suitable for manufacturing the hydroactivated layer and the wall comprise inert inorganic solvents that do not adversely harm the materials, the capsule and the final, laminated wall, hydro-activated layer. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride nitroethane, nitropropane tetrachloroethane, ethyl ether, isopropyl ether, cyclohexane, cyclooctane, benzene, toluene, naphtha, 1,4-dioxane, tetrahydrofuran, diglyme, water, aqueous solvents containing inorganic salts such as sodium chloride, calcium chloride, and the like, and mixtures thereof such as acetone and water, acetone and methanol, acetone and ethyl alcohol, methylene dichloride and methanol, and ethylene dichloride and methanol.

The semipermeable wall and the subcoat of the dosage form can be formed in one technique using the air-suspension procedure. This procedure consists of suspending and tumbling the bilayer core in a current of air, an inner subcoat composition and an outer semipermeable wall forming composition, until, in either operation, the subcoat and the outer wall coat is applied to the bilayer core. The air-suspension procedure is well suited for independently forming the wall of the dosage form. The air-suspension procedure is described in U.S. Pat. No. 2,799,241; in *J. Am, Pharm. Assoc.*, Vol. 48, pp. 451–459 (1959); and, ibid., Vol. 49, pp. 82–84 (1960). The dosage form also can be coated with a Wurster® air-suspension coater using, for example, methylene dichloride methanol as a cosolvent. An Aeromatic® air-suspension coater can be used employing a cosolvent. Other coating techniques, such as pan coating, can be used for providing the dosage form. In the pan coating system, the subcoat on the wall-forming compositions is deposited by successive spraying of the respective compensation on the bilayered core accompanied by tumbling in a rotating pan. A pan coater is used because of its availability at commercial scale. Other techniques can be used for coating the drug core. Finally, the wall or coated dosage form are dried in a forced-air oven at 40° C. for 1 week, or in a temperature and humidity controlled oven for 24 hours at 40° C. and 50% relative humidity, to free the dosage form of solvent.

The dosage form of the invention is manufactured by standard techniques. For example, in one manufacture the beneficial drug and other ingredients comprising the first layer facing the exit means are blended and pressed into a solid layer. The layer possesses dimensions that correspond to the internal dimensions of the area the layer is to occupy in the dosage form, and it also possesses dimensions corresponding to the second layer for forming a contacting arrangement therewith. The drug and other ingredients can also be blended with a solvent and mixed into a solid or semisolid form by conventional methods, such as ballmilling, calendering, stirring or rollmilling, and then pressed into a preselected shape. Next, a layer of osmopolymer composition is placed in contact with the layer of drug in a like manner. The layering of the drug formulation and the osmopolymer layer can be fabricated by conventional two-layer press techniques. The two contacted layers are first coated with a subcoat and an outer semipermeable wall. The air-suspension and air-tumbling procedures comprise in suspending and tumbling the pressed, contacting first and second layers in a current of air containing the delayed-forming composition until the first and second layers are surrounded by the wall composition.

In another manufacture, the dosage form is manufactured by the wet granulation technique. In the wet granulation technique, the drug and the ingredients comprising the first layer or drug composition are blended using an organic solvent, such as denatured anhydrous ethanol, as the granulation fluid. The ingredients forming the first layer or drug composition are individually passed through a preselected screen and then thoroughly blended in a mixer. Next, other ingredients comprising the first layer can be dissolved in a portion of the granulation fluid, such as the solvent described above. Then, the latter prepared wet blend is slowly added to the drug blend with continual mixing in the blender. The granulating fluid is added until a wet blend is produced, which wet mass blend is then forced through a predetermined screen onto oven trays. The blend is dried for 18 to 24 hours at 24° C. to 35° C. in a forced-air oven. The dried granules are then sized. Next, magnesium stearate is added to the drug granulation, then put into milling jars and mixed on a jar mill for 10 minutes. The composition is pressed into a layer, for example, in a Manesty® press. The speed of the press is set at 20 rpm and the maximum load set at 2 tons. The first layer is pressed against the composition forming the second layer and the bilayer tablets are fed to the Kilian® Dry Coater press and surrounded with the drug-free coat, followed by the exterior wall solvent coating.

Another manufacturing process that can be used for providing the compartment-forming composition comprises blending the powdered ingredients in a fluid bed granulator. After the powdered ingredients are dry blended in the granulator, a granulating fluid, for example, poly (vinylpyrrolidone) in water, is sprayed onto the powders. The coated powders are then dried in the granulator. This process granulates all the ingredients present therein while adding the granulating fluid. After the granules are dried, a lubricant, such as stearic acid or magnesium stearate, is mixed into the granulation using a V-blender. The granules are then pressed in the manner described above.

METHOD OF PRACTICING THE INVENTION

The invention provides a process for the substantially uniform and nonvarying rate of release of a drug from a dosage form. The term "substantially" indicates a 100% drug delivery rate ±5% variation from the norm. The dosage form comprises a composition, a dose of drug in the composition, and a hydrophilic polymer in the composition, and wherein the process comprises (1) formulating the composition with a drug possession, a particle size up to and including 150 µm, and (2) formulating the composition with a hydrophilic polymer possessing a particle size up to and including 250 µm, whereby, through the copresence of (1) and (2) in the composition, the drug is delivered at a uniform and nonvarying rate of release from the dosage form.

The invention also provides a process for substantially uniform and nonvarying rate of release of a drug from a dosage form. The expression "uniform" as used for the purpose of this invention means a deviation of ±5% from a constant, 100%, nonvarying delivery. The dosage form comprises a composition, a dose of drug in the composition, a hydrophilic polymer in the composition, and a separate composition for displacing the drug composition from the dosage form. The process comprises: (1) formulating the composition with a drug possessing a particle size up to and including 150 µm; and (2) formulating the composition with a hydrophilic polymer possessing a particle size up to and including 150 µm, whereby, through the copresence of (1) and (2), in combination with the composition for displacing the drug composition imbibing fluid, expands and displaces the drug composition from the dosage form. The drug is delivered at a substantially uniform and nonvarying rate of release over time.

The invention also comprises a method for delivering a drug to a patient. The method comprises: (A) admitting orally into the patient a dosage form comprising: (1) a semipermeable wall that surrounds and forms a compartment; (2) a drug composition in the compartment; (3) a dose of drug particles up to 150 µm in the drug composition; (4) a hydrophilic polymer of up to 250 µm in the drug composition; and (5) an exit in the semipermeable wall; (B) imbibing fluid through the semipermeable wall into the drug composition, whereby, through the co-action of (2), (3) and (4), a dispensable drug composition is formed in the dosage form; and (C) delivering the drug composition through the exit to a patient at a substantially uniform and nonvarying dose over time.

The invention further comprises a method for providing a drug-free interval by placing a subcoat in the dosage form in contact with the inside surface of the semipermeable wall and surrounding the drug composition, or surrounding both a drug composition and a push composition, which drug-free interval is followed in 2 to 5 hours by a drug delivery period of 1 to 15 hours. The latter method is indicated for the treatment of hypertension and angina as it provides a drug-free interval when a patient is less active, such as at rest or when asleep, and the inventive method then provides drug during the rising and waking hours, mainly during the time when activity reaches a maximum during the daytime hours.

The method of the invention pertains also to the management of blood pressure, the management of the systemic physiology, and to the management of chronotherapy, that is, timetherapy, by administering a drug according to the mode and the manner of the invention.

The novel dosage form of this invention uses dual means for the attainment of precise release rates of drugs that are difficult to deliver in the environment of use, while simultaneously maintaining the integrity and the character of the system. While features and advantages of the invention have been described and pointed out as applied to the present embodiments, those skilled in the dispensing art will appreciate that various modifications, changes, additions and omissions in the system illustrated and described herein can be made without departing from the spirit of the invention.

We claim:

1. A process for providing a controlled drug rate of release from a dosage form, wherein the dosage form comprises a composition, a dose of drug in the composition, and a hydrophilic polymer in the composition; and wherein the process comprises (1) formulating the composition with a drug possessing a size less than 150 µm, and (2) formulating the composition with a hydrophilic polymer of less than 250 µm size; whereby, through the copresence of (1) and (2) in the composition, the drug is delivered at a controlled rate of release from the dosage form.

2. The process for providing the dosage form according to claim 1, wherein the composition is enveloped by a wall comprising means for releasing the drug from the dosage form.

3. The process for providing the dosage form according to claim 1, wherein the composition is surrounded by an outer wall and an inner subcoat, with means in the dosage form for releasing the drug from the dosage form.

4. A process for providing a controlled drug rate of release from a dosage form, wherein the dosage form comprises: a drug composition comprising a dose of drug and a hydrophilic polymer, and a dispensing, composition comprising means for dispensing the drug composition from the dosage form; and wherein the process comprises formulating the drug composition with a drug possessing a particle size up to 150 µm and with a hydrophilic polymer possessing a particle size up to 250 µm, which, through the cooperation of the drug particles and the hydrophilic polymer particles, and the dispensing composition assisting the drug composition, the drug is delivered at a substantially controlled rate of release from the dosage form.

5. The process for providing the drug rate of release according to claim 4, wherein the hydrophilic polymer particle cooperates with the drug particle as a pharmaceutical carrier for delivering the drug from the dosage form.

6. The process for providing the drug rate of release according to claim 4, wherein the dispensing composition assists in displacing the drug composition from the dosage form.

7. The process for providing the drug rate of release according to claim 4, wherein a wall encases both the drug composition and the dispensing composition, and comprises means for releasing the drug from the dosage form.

8. The process for providing the drug rate of release according to claim 4, wherein a wall surrounds the drug composition and the dispensing composition, a subcoat is between the wall, the drug composition and the dispensing composition, and the dosage form comprises exit means for releasing the drug from the dosage form.

9. A dosage form for the delivery of a drug, wherein the dosage form comprises:
 (a) a composition comprising:
 (b) a dose of drug in the composition said drug comprising a size less than 150 µm;
 (c) a hydrophilic polymer in the composition, said polymer comprising a size less than 250 µm;
 (d) a wall comprising a composition permeable to the passage of fluid that surrounds the composition comprising the dose of drug and the hydrophilic polymer; and
 (e) means in the wall for delivering the drug at a substantially controlled rate from the dosage form.

10. A dosage form for the delivery of a drug, wherein the dosage form comprises
 (a) a drug composition;
 (b) a dose of drug comprising a size of less than 150 µm in the drug composition;
 (c) a hydrophilic polymer comprising a size of less than 250 µm in the drug composition;
 (d) a coat that surrounds the drug composition comprising means for delaying release of drug from the drug composition;
 (e) a wall comprising a composition that surrounds the coat; and,
 (f) means in the dosage form for delivering the drug from the dosage form.

11. The dosage form according to claim 10, wherein the drug is a member selected from the group consisting of verapamil, nifedipine, milvadipine, flunarizine, nimodipine, diltiazem, nicardipine, nitrendipine, nisoldipine, felodipine, amlodipine, isradipine, cinnarizine, fendiline, ramipril, fusinopril, altiopril, benazepril, livenzapril, alacepril, cilazapril, cilazaprilat, perindopril, zofenopril, enalapril, lisinopril, imidapril, spirapril, rentiapril, captopril, delapril, olindapril, indolapril, and quinapril.

12. A dosage form for the delivery of a drug, wherein the dosage form comprises:
 (a) a drug composition comprising a drug comprising a particle of less than 150 µm size and a pharmaceutically acceptable hydrophilic polymer carrier comprising a particle of less than 250 µm size;
 (b) a displacement composition in contact with the drug composition comprising means for causing fluid to enter the displacement composition, whereby the displacement composition increases in volume and displaces the drug composition from the dosage form;
 (c) a wall, comprising means for permitting a fluid to enter the dosage form, that surrounds the drug composition and the displacement composition; and
 (d) means in the wall for delivering the drug as a substantially constant rate over a dispensing time.

13. The dosage form for delivering the drug according to claim 12, wherein the drug is a member selected from the group consisting of a calcium channel blocker, an angiotensin enzyme inhibitor, alpha receptor blocking drugs, beta receptor blocking drugs, antianginal drugs, antiarrhythmias drugs, antiembolus drugs, antihypertensive drugs, digitalis drugs, hemorheologic drugs, inotropic drugs, myocardial infarction prophylasix drugs, cerebral vasodilators, coronary vasodilators, peripheral vasodilators and vasopresor drugs.

14. A dosage form for delivering a drug orally to a patient in need of a drug, wherein the dosage form comprises:
 (a) a drug composition comprising a drug comprising a particle size up to and including 150 µm, and a hydrophilic polymer carrier for the drug comprising a particle size up to and including 250 µm;
 (b) a displacement composition in contrast with the drug composition comprising a polymer that expands in the presence of fluid for displacement of the drug composition from the dosage form;
 (c) a coat, free of drug, which surrounds the drug and the displacement composition for slowing the passageway of fluid into the dosage form;
 (d) a wall tha surrounds the coat and is permeable to the passage of fluid; and,
 (e) means in the dosage form for delivering the drug from the dosage form at a substantially constant rate over time.

15. The dosage form for delivering the drug according to claim 14, wherein the drug composition comprises a member selected from the group consisting of an antioxidant and a surfactant.

16. The dosage form for delivering the drug according to claim 14, wherein the drug in the drug is a member selected from the group consisting of verapamil, isradipine, nifedipine, nilvadipine, flunarizine, nimodipine, diltiazem, nicardipine, nitrendipine, nisoldipine, felodipine, amlodipine, cinnarizine, fendiline, prazosin, clonidine, pinacidil, alfuzosin, quinapril, indolapril, olindapril, delapril, captopril, rentrapil, spirapril, imidapril, lisinopril, enalapril, enalaprilat, zofenopril, perindopril, cilazaprilat, alacepril, libenzapril, benazepril, altropril, fosinopril and ramipril.

17. A method for the management of blood pressure in a patient, wherein the method comprises:
 (a) admitting orally into the patent a therapeutic composition comprising a dose of drug indicated for the management of blood pressure with the drug possessing a particle size of less than 150 µm, and a pharmaceutically acceptable hydrophilic carrier for the drug possessing a particle size of less than 250 µm; and,
 (b) managing the blood pressure by codelivering the drug and the accompanying polymer at a substantially constant rate of release from the composition to provide an effective dose for managing the blood pressure of the patient.

18. The method for the management of blood pressure according to claim 17, wherein a wall with means for providing a passage therethrough surrounds the therapeutic composition.

19. The method for the management of blood pressure according to claim 17, wherein a coat comprising a hydroxyalkylcellulose surrounds the therapeutic composition and a wall comprising a member selected from cellulose ester, cellulose ether and cellulose ester-ether surrounds the coat, with means in the coat and in the wall for delivering the drug and polymer from the composition.

20. The method for the management of blood pressure according to claim 17, wherein the drug is a member selected from the group consisting of alpha-receptor, beta-receptor, antihypertensive, alpha-blocker, beta-blocker, calcium channel blocker, angiotensin enzyme inhibitor, vasodilator, cerebral, coronary, peripheral, and alpha adrenergic drugs.

21. A method for the management of the systemic physiology of a patient, wherein the method comprises:
   (a) admitting orally into the patient a therapeutic composition comprising a dose of drug indicated for the management of a systemic physiology with the drug possessing an average particle size of less than 150 μm, and a therapeutically acceptable hydrophilic polymer possessing an average particle size of less than 250 μm for delivering the drug from the therapeutic composition; and a delivery composition in contact with the therapeutic composition comprising a therapeutically acceptable hydrophilic polymer possessing a greater number-average molecular weight than the hydrophilic polymer present in the therapeutic composition for aiding in delivering the drug from the therapeutic composition; and,
   (b) managing the systemic physiology of the patient by the codelivery of the drug and the polymer at a substantially constant rate of release from the therapeutic composition aided by the delivery composition to provide an effective dose for the management of the systemic physiology of the patient.

22. The method for the management of the systemic physiology of a patient according to claim 21, wherein a wall with means for providing a passage therethrough surrounds the therapeutic composition and the delivery composition.

23. The method for the management of the systematic phisiology of a patient according to claim 21, wherein an inner coat surrounds both the therapeutic composition and the delivery composition, and an outer wall surrounds the inner coat, with means in the coat and wall for delivery of the drug from the therapeutic composition.

24. The method for the management of the systemic physiology of the patient according to claim 21, wherein the management of the systemic physiology comprises administering a drug comprising vasodilating, hypotensive, and antianginal therapy.

25. The method for the management of the systemic physiology of the patient according to claim 21, wherein the management of the systemic physiology comprises administering a drug for alleviating angiotensin related hypertension in the patient.

26. A method of timetherapy for delivering a drug to a patient at a selected time, wherein the method comprises administering orally to the patient a therapeutic composition comprising a dose of drug possessing an average particle size up to 150 μm and a pharmaceutically acceptable polymer possessing an average particle size up to 250 μm, and means for governing the release of drug from the therapeutic composition, whereby the drug is released by the means in a substantially constant rate of release at the selected time for timetherapy.

27. A method for timetherapy for delivering a drug to a patient over a selected time for the management of hypertension, wherein the method comprises orally administering to the patient a therapeutic composition comprising a calcium channel blocker drug and an angiotensin converting enzyme inhibitor drug possessing an average particle size up to 150 μm and a pharmaceutically acceptable polymer possessing an average particle size up to 250 μm, and means for governing the release of the drugs from the therapeutic composition, whereby the drugs are timed-release in a substantially constant dose over the selected time for the timetherapy management of hypertension.

28. The method of timetherapy for delivering a drug to a patient according to claim 27, wherein the calcium channel blocker is a member selected from the group consisting of nifedipine, isradipine, nilvadipine, verapril, flunarizine, nimodipine, diltiazem, nicardipine, norverapamil, nitrendipine, nisoldipine, felodipine, amlodipine, cinnarizine, fendiline, ramipril, fosinopril, altiopril, benazepril, libenzapril, alacepril, cilazapril, cilazaprilat, perindopril, zofenopril, enalapril, lisinopril, imidapril, spirapril, rentiapril, captopril, delapril, alindapril, indolapril, and quinapril.

29. The method of timetherapy for the delivery of a drug to a patient according to claim 27, wherein the method comprises administering a drug pair to the patient in a hypertension pressure lowering effective dose, and wherein the drug pair comprises diltiazem and captopril.

30. The method of timetherapy for the delivery of a drug to a patient according to claim 27, wherein the therapeutic composition comprises a member selected from the group consisting of an antioxidant, and a surfactant.

31. The method of timetherapy for the delivery of a drug to a patient according to claim 27, wherein the timetherapy delays the delivery of drug for 2 to 6 hours and then delivers the drug for up to 15 hours.

* * * * *